United States Patent [19]

Stevens

[11] 4,341,224
[45] Jul. 27, 1982

[54] CATHETER FLUSHING APPARATUS

[75] Inventor: Jerry D. Stevens, Thousand Oaks, Calif.

[73] Assignee: Gould Inc., Rolling Meadows, Ill.

[21] Appl. No.: 118,420

[22] Filed: Feb. 4, 1980

[51] Int. Cl.³ .............................................. A61B 5/02
[52] U.S. Cl. .................................. 128/675; 128/673; 128/214 E; 137/238; 251/117
[58] Field of Search ........... 128/214 E, 214 F, 214 R, 128/675, 274, DIG. 12, DIG. 13, 672-674; 251/117; 137/238

[56] References Cited

U.S. PATENT DOCUMENTS

| | | | |
|---|---|---|---|
| 1,005,409 | 10/1911 | Bruns | 251/117 X |
| 2,411,667 | 11/1946 | Mowrey | 251/117 X |
| 2,655,170 | 10/1953 | Ferguson | 251/117 X |
| 2,955,614 | 10/1960 | Meynig | 251/117 X |
| 3,298,367 | 1/1967 | Bergman | 128/214 R |
| 3,474,816 | 10/1969 | Burgess | 137/238 |
| 3,675,891 | 7/1972 | Reynolds et al. | 251/117 |
| 3,877,428 | 4/1975 | Seagle et al. | 128/214 R |

*Primary Examiner*—Kyle L. Howell

[57] ABSTRACT

A flow control apparatus having a flow passage with an inlet and outlet is provided in a housing. A control means having a conical valve seat and ball member for restricting flow through the seat is provided in the inlet of the passage. A valve plunger slidably located within the housing is resiliently biased against a second valve seat provided in the passage walls of the housing. The plunger includes a marine bore capillary passage which effectively bypasses the second valve seat, thus permitting a first low flow. When the plunger is moved from its seat, a second higher flow is established for flushing the device. This second higher flow rate is controlled by valve control means in the inlet of the passage to prevent excessively high flow rates.

10 Claims, 3 Drawing Figures

CATHETER FLUSHING APPARATUS

BACKGROUND AND SUMMARY OF INVENTION

The present invention relates to the flow control apparatus, especially those for use in fluid flow catheters of the type found in blood pressure and dynamic measurement systems. In such systems, a catheter commonly is inserted into a patient's vessel to a location where measurements are desired. The catheter is maintained full of a neutral, sterile solution, which actually flows into the patient at a very low rate of, say, 3 ml/hr. This low flow is required to keep the catheter open, or patent, throughout its length, by preventing the ingress of blood constituents at the in-dwelling end of the catheter. By monitoring changes in the liquid pressure in the catheter, a variety of useful data can be obtained regarding the blood pressure, flow, etc. at the in-dwelling end.

When such catheters are prepared for use, they must be flushed completely out of all air which could be harmful to the patient. Since the normal small flow rate would require such a long time for filling and flushing operations, prior art devices have made provisions for providing for much higher flow rates (rapid or fast flush mode) for use during the initial filling and flushing of the catheter and for use to momentarily allow a higher flow rate into the patient to clear out any debris which may have collected at the in-dwelling end of the catheter. U.S. Pat. No. 3,675,891 issued July 12, 1972 as well as copending application entitled Improved Catheter Flushing Apparatus, Ser. No. 06/52,019, assigned to the assignee of the instant application, disclosed such catheter flushing apparatus. These prior art devices in operation under the fast flush mode of operation, however, have suffered from the defect of possible production of air bubbles in the drip chamber of the measurement system if the operator is not careful. These bubbles which can enter the patient line pose a danger to the patient and grossly degrade the dynamic performance of this measuring system. The bubbles are generated by the Venturi effect of this high velocity jet of liquid flowing under rapid flush mode.

OBJECTS OF THE INVENTION

A primary object of this invention is to provide an improved catheter flushing apparatus which is highly reliable and safe in operation.

Another object of this invention is to provide such an apparatus in combination with a pressure transmitting diaphragm assembly.

A further object of the invention is to provide such an apparatus with provision for overpressure release, to prevent damage to associated pressure instrumentation.

A further object of the invention is to provide such an apparatus which is suited for simple single handed actuation.

Still a further object of the invention is to provide such an apparatus which can be emptied of solution easily.

Yet still another object of the invention is to provide such an apparatus which is inexpensive in construction and economically disposable following use.

These objects are given only by way of example; thus other desirable objectives and advantages inherently achieved by the disclosed invention may occur to those skilled in the art. Nonetheless, the scope of this invention is to be limited only by the appended claims.

SUMMARY OF THE INVENTION

The above objects and other advantages are achieved by the invention, in which a flow passage having an inlet and outlet is provided in a housing. A control means having a conical inlet valve seat and ball member for restricting flow through the seat is provided in the inlet of the passage. A valve plunger slidably located within the housing is resiliently biased against another seat provided in the passage walls of the housing. The plunger includes a capillary passage which effectively bypasses the second valve seat, thus permitting a first, low flow. When the plunger is moved from its seat, a second higher flow is established for flushing the device and its associated catheter. This second higher flow rate is controlled by valve control means in the inlet of the passage to prevent excessively high flow rates and the associated generation of air bubbles in the measurement systems.

In one embodiment, the downstream end of the flow passage opens into a plenum bounded on its lower end by a flexible pressure transmitting diaphragm. The plenum is oriented and configured relative to the flow passage so that air in the plenum is easily flushed out during fill prior to use.

DETAILED DESCRIPTION OF THE PREFERRED EMBODIMENTS

Figure 1:
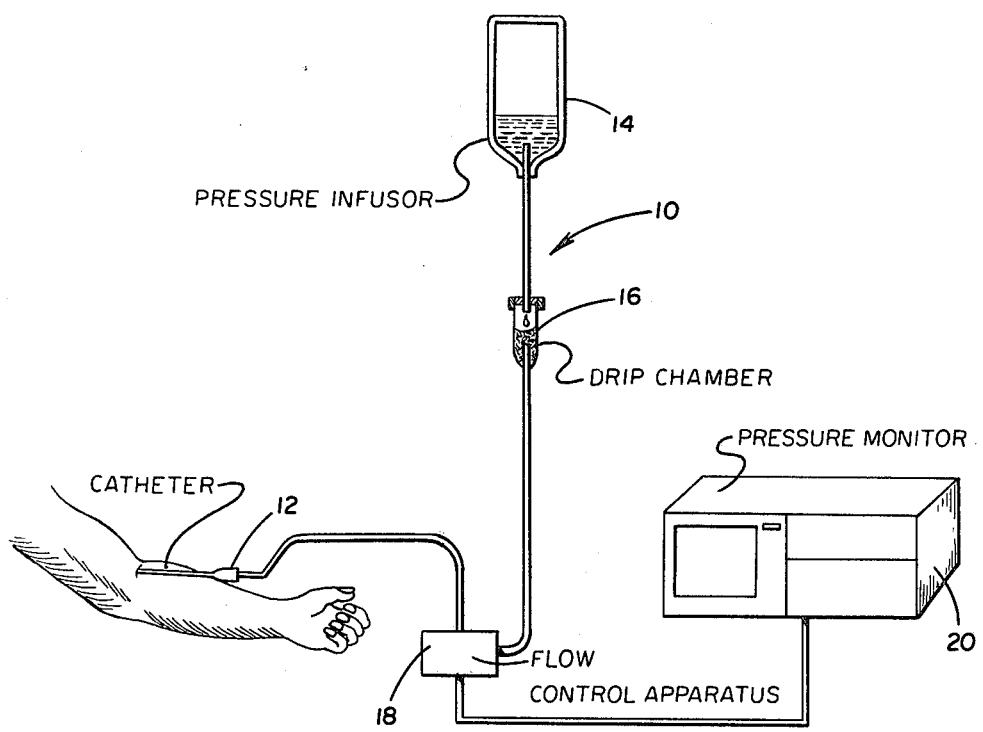
FIG. 1 shows a diagrammatical view of flow chart control apparatus of the invention in a dynamic measurement system.

The following is a detailed description of the preferred embodiments of the invention, reference being made to the drawing in which like reference numerals identify like elements of structure in the Figures.

FIG. 1 shows a diagrammatical view of a hemodynamic measurement system 10 of a pressure infusor 14, a drip chamber 16, a flow control apparatus 18 and a pressure monitor 20. Flow control apparatus 18 controls the flow from the pressure infusor 14 via drip chamber 16 to the patient through the catheter 12. A monitor 20 operatively connected to the catheter is provided for recording a variety of useful data such as blood pressure, etc.

Figure 2:
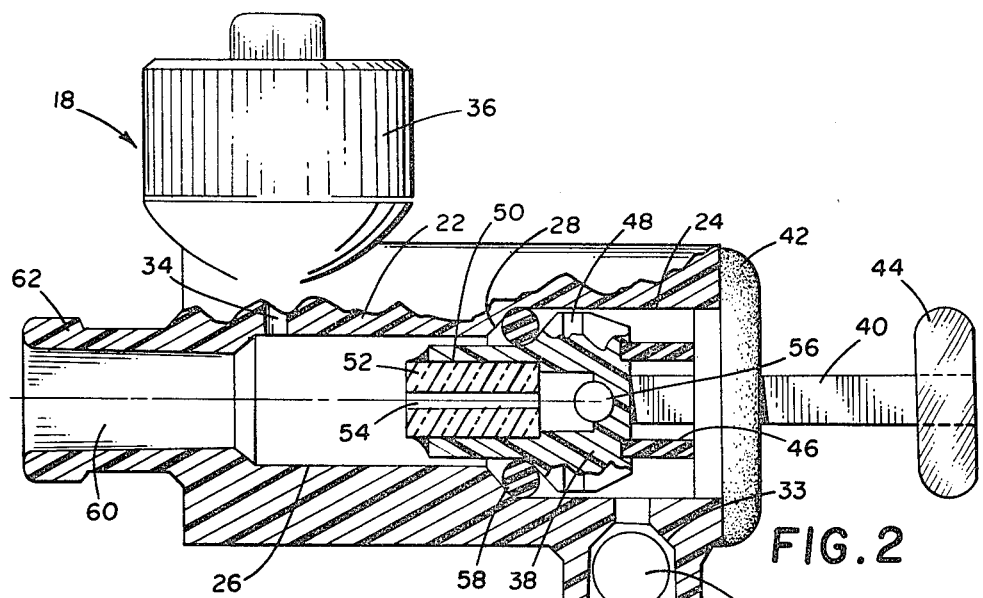
FIG. 2 shows an elevational view, partially in section, of one embodiment of the invention.

FIG. 2 shows an elevational view, partially in section, of one embodiment of a flow control apparatus 18 according to the invention. An essentially cylindrical housing 22 is provided with a first, larger interior bore or chamber 24 and a second smaller interior bore 26, the two bores being joined by a conical valve seat 28 to provide a flow passage. An inlet passage 30 enters bore 24 from below, as illustrated, and is provided with a boss having a conventional attachment fitting 32. At the entrance of inlet passage 30 into bore 24 is an inlet passage conical valve seat 33 with valve control member 35 preferably of the ball type for restricting the flow as will be further explained below. The geometry of the valve seat and corresponding valve member 35 is provided to partially restrict the flow entering bore 24 but never to seal off the flow from passage 30 to bore 24. The inlet passage additionally preferably has a retaining ring 37 to hold control valve member 35 as may be needed while clearing the apparatus of a trapped air bubble as will be further explained below. An outlet passage 34 leaves bore 26 and is provided with a boss having a conventional attachment fitting 36. Housing 22 preferably is injection molded from a material such as clear polycarbonate plastic.

A valve plunger 38 is slidably mounted within bore 24. An actuator shaft 40 extends from the inlet end of valve plunger 38 through a hole provided in cap 42. An actuator knob or button 44 is provided on the outer end of shaft 40. A short, resilient spring cylinder 46 of a material such as silicone rubber is captured between and sealed to valve plunger 38 and cap 42. Spring cylinder 46 is sized so that when the apparatus is assembled as shown, valve plunger 38 is resiliently biased toward valve seat 28. The spring constant of spring cylinder 46 is chosen so that should the pressure at the outlet end of the apparatus approach an undesirably high level for the pressure transducer operatively connected thereto the valve plunger 38 will move to the right to help equalize the pressure. Plunger 38 further includes a radially extending circumferential flange 48, which is sufficiently smaller in diameter than bore 24 to allow the desired liquid flow through the apparatus. The outlet end of valve plunger 38 is provided with a counterbore 50, in which a glass cylinder 52 is secured by suitable means. A capillary bore 54 is provided in cylinder 52, the bore diameter being chosen to provide the desired continuous flow rate through the apparatus in actual use. At the bottom of counterbore 50, one or more radially extending passages 56 are provided which open into bore 24 on the inlet side of circumferential flange 48, to complete the continuous, low flow path through the apparatus. The outlet side of circumferential flange 48 is provided with a conical surface of geometry similar to that of valve set 28. A resilient seal ring 58 of a material such as silicone rubber is captured between valve plunger 38 and seat 28. Ring 58 preferably is sized so that it moves with valve plunger 38 and is small enough in outer diameter to allow a desired second higher flush flow rate when valve plunger 38 is moved to the right, as illustrated, However, ring 58 also may be sized to fit snugly in bore 24 right at seat 28, in which case the inner diameter of the ring is sized to allow the second desired higher flush rate. Finally, an auxiliary outlet passage 60 is provided through a boss having an attachment fitting 62, to which suitable pressure instrumentation is attached during use.

Figure 3:
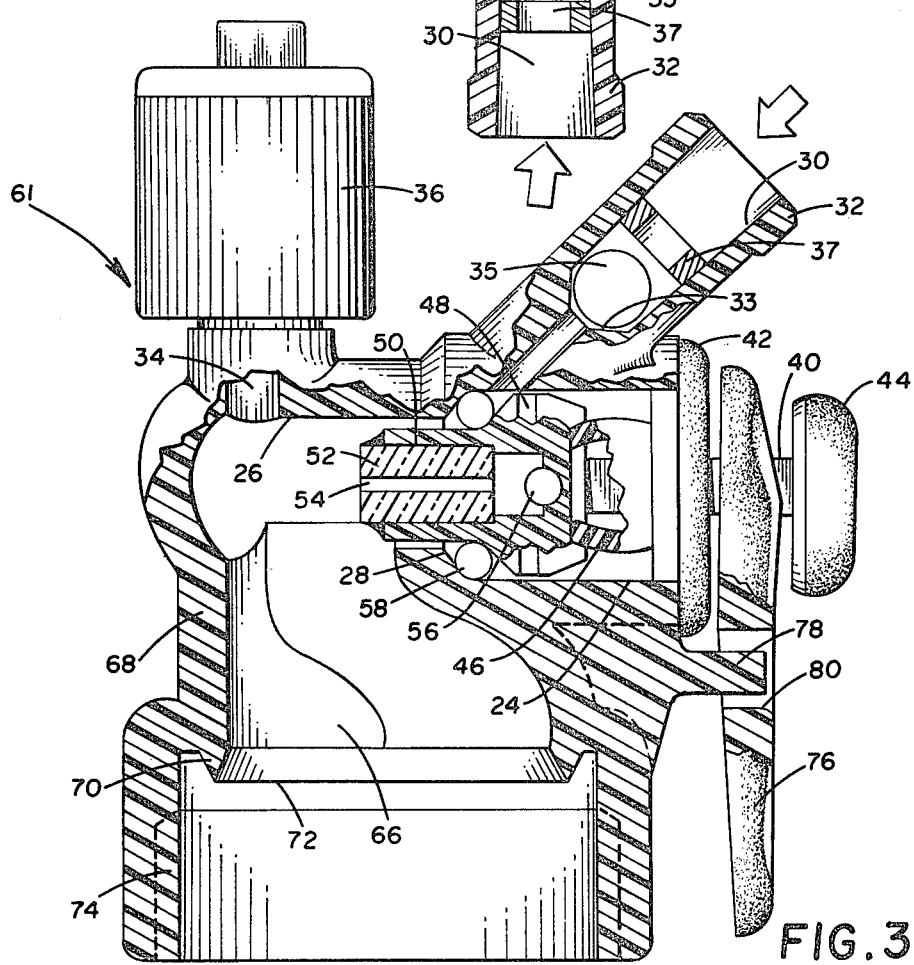
FIG. 3 shows an elevational view, partially in section, of another embodiment of the invention in which a pressure transmitting diaphragm is built into the apparatus.

FIG. 3 shows an elevational view, partly in section, of another embodiment 61 of a flow control device according to the invention. Here, the apparatus 61 is identical to the embodiment of FIG. 2 except inlet passage 30 enters from the top and outlet passage 26 opens downwardly, as illustrated, into a plenum 66 bounded by downwardly depending, generally outwardly flaring circumferential wall 68. The lower edge of wall 68 defines an annular lip 70 which is hermetically attached to a thin, flexible plastic diaphragm 72. Thus, liquid in plenum 66 causes diaphragm 72 to flex in response to pressure changes. These changes are transmitted to a liquid on the other side of diaphragm 72. The pressure in this other liquid is monitored by a transducer, not shown, attached to the apparatus by a suitable fitting 74. For simple actuation of the apparatus to provide high flush flow, a flush lever 76 is slidably mounted on actuator shaft 40. A retaining finger 78 extends from housing 22 into a bore 80 in lever 76, to keep the lever in position for convenient actuation.

In opertion, appartus 10 as shown in FIG. 1 is connected to receive liquid through inlet passage 30. The force of this fluid flow in passage 30 keeps control valve member 35 in contact with inlet passage valve seat 33 thereby partially restricting the flow into bore 24. This partially restricted flow rate is, however, always greater than that needed to provide for a continuous flow at the low flow rate for the device. The liquid then flows from bore 24 through passages 56 and through capillary bore 54 and then out outlet passage 34.

When used in the fast flush mode or second higher flush rate such as to speed flushing of air from the device prior to insertion of the catheter in a patient, actuator shaft 40 is moved to the right from the position shown in FIG. 2, thus permitting fluid to flow around valve plunger 38 and thereby allowing for larger flow rate to sweep air from the apparatus. Once the apparatus has been flushed and the catheter has been inserted into a patient, slow continuous flow rate is provided using capillary bore 54. Periodically, to ensure that the in-dwelling end of the catheter does not clog, the actuator rod 40 is moved to activate the fast flow mode to provide a short, high burst of fluid through the system, thereby dislodging and sweeping away any undesirable particles. This fast flush flow mode can cause the generation of bubbles of air in the drip chamber of the measurement system if the flow rate is too high. It is the flow control means 35 in the inlet passage that prevents too high a flow rate from occuring. The inlet flow control means provides for allowing sufficient flow rates for the normal flow rate and additionally to allow for the second higher flush rate, but the flow control does not allow the high flush rate to be of such magnitude so as to cause air bubble generation in the system. That is, the flow control means is calibrated to allow for fast flushing or dislodging of undesirable particles but not so high as to cause the generation of bubbles in the air chamber. In the event that an air bubble becomes lodged in the apparatus, the apparatus can be disconnected from the system and inverted, if necessary, (see FIG. 3) so that ball member 35 moves out of engagement with valve seat 33 and rests on retaining ring 37 to allow removal of the air bubble. Without this feature of the retaining ring to maintain the ball member in the inlet and still provide a high flow rate the apparatus might well have to be discarded if such a bubble were to form.

In use, the apparatus of FIG. 3 operates virtually identically to that of FIG. 2. High flush flow is easily provided with one hand by gripping housing and lever 76 between the thumb and forefinger and squeezing. Due to the downwardly flaring geometry of plenum 66 and the location of outlet passage 26 at the upper end thereof, air in plenum 66 is quickly and efficiently flushed from the device prior to insertion of the catheter in the patient.

In view of the above it will be seen that the several objects of the invention are achieved and other advantageous results attained.

As various changes could be made in the above apparatus without departing from the scope of the invention, it is intended that all matter contained in the above description shall be interpreted as illustrative and not in a limiting sense. For example, a flapper valve type construction might be used for flow control in the inlet passage.

Having described my invention in sufficient detail to enable those skilled in the art to make and use it, I claim:

1. An improved flow control apparatus for use in liquid flow systems for pressure monitoring of hemodynamics, such systems including a catheter which is continuously flushed in use, said apparatus comprising:
a housing having at least one passage therein, said passage having an inlet and an outlet;
a valve seat defined in said passage;
a valve plunger movably mounted in said passage;
resilient means biasing said plunger into contact with said seat;
capillary means extending at least partially through said plunger for providing a low flow path from said inlet to said outlet when said valve plunger is in contact with said valve seat;
means for selectively moving said valve plunger out of contact with said valve seat to provide a high flow path around said plunger from said inlet to said outlet;
said moving means including an actuator member attached to said plunger and slidably mounted in and extending through a hole extending from said passage to the exterior of said housing so that said plunger may be moved selectively out of contact with said seat by manipulation of said actuator member from externally of said housing; and
a flexible sealing element connected about said actuator member and to said housing about said hole to prevent liquid from leaking out of said passage through said hole; and
said inlet having flow control means to limit the amount of flow in said high flow path thereby minimizing the possible production of air bubbles in the system.

2. An improved flow apparatus according to claim 1 wherein said flow control means includes a second valve seat and ball member.

3. An improved flow apparatus according to claim 2 wherein said inlet has a retaining means for holding said ball member.

4. An improved flow control apparatus according to claim 1, wherein said housing comprises a plenum extending downwardly from said at least one passage, said plenum having a flexible lower diaphragm wall; and further comprising means located exteriorly of said diaphragm for attaching a pressure sensing device.

5. An improved flow control apparatus according to claim 4, wherein said plenum comprises downwardly extending, essentially smoothly flaring side walls, whereby gas trapped in said plenum is caused to rise as said plenum fills with liquid, to be flushed from the apparatus through said outlet.

6. An improved flow control apparatus according to claim 1, wherein said valve plunger comprises an essentially cylindrical body with an essentially radially extending circumferential flange thereon, a counterbore extending axially through said cylindrical body, said capillary means being mounted in said counterbore, and at least one passage extending from said counterbore outward to an exterior surface of said cylindrical body.

7. An improved flow control apparatus according to claim 6, further comprising a resilient seal element positioned between said circumferential flange and said valve seat.

8. An improved flow control apparatus according to claim 7, wherein said seal element is a resilient ring having an outer diameter sized to permit flow of liquid through said passage when said valve plunger has been moved out of contact with said valve seat.

9. An improved flow control apparatus according to claim 7, wherein said seal element is a resilient ring having an inner diameter sized to permit flow of liquid through said passage when said valve plunger has been moved out of contact with said valve seat.

10. An improved flow control apparatus according to claim 1, wherein said moving means further includes a contact button mounted on the end of said actuator member extending to the exterior of said housing and lever means movably mounted on said housing in position to cooperate with said button to move said valve plunger out of contact with said valve seat.

* * * * *